United States Patent
Maile et al.

(10) Patent No.: US 10,434,300 B2
(45) Date of Patent: Oct. 8, 2019

(54) IMPLANTABLE MEDICAL DEVICE WITH STACKED CIRCUIT COMPONENTS

(71) Applicant: Cardiac Pacemaker, Inc., St. Paul, MN (US)

(72) Inventors: Keith R. Maile, New Brighton, MN (US); John M. Edgell, Plymouth, MN (US); Mathew L. Gilk, Brooklyn Park, MN (US); Brian L. Schmidt, White Bear Lake, MN (US); Benjamin J. Haasl, Forest Lake, MN (US); James E. Blood, Shoreview, MN (US)

(73) Assignee: Cardiac Pacemaker, Inc., St. Paul, MN (US)

( * ) Notice: Subject to any disclaimer, the term of this patent is extended or adjusted under 35 U.S.C. 154(b) by 293 days.

(21) Appl. No.: 14/953,987

(22) Filed: Nov. 30, 2015

(65) Prior Publication Data

US 2016/0151621 A1 Jun. 2, 2016

Related U.S. Application Data

(60) Provisional application No. 62/086,015, filed on Dec. 1, 2014.

(51) Int. Cl.
*A61N 1/00* (2006.01)
*A61N 1/02* (2006.01)
(Continued)

(52) U.S. Cl.
CPC ............... *A61N 1/025* (2013.01); *A61N 1/05* (2013.01); *A61N 1/36514* (2013.01); *A61N 1/3758* (2013.01); *A61N 1/3756* (2013.01)

(58) Field of Classification Search
CPC ...... A61N 1/3758; A61N 1/025; A61N 1/362; A61N 1/3756
See application file for complete search history.

(56) References Cited

U.S. PATENT DOCUMENTS 5,571,146 A 11/1996 Jones et al.
5,944,744 A 8/1999 Paul et al.
(Continued)

FOREIGN PATENT DOCUMENTS

JP 2004176818 A 6/2004
JP 2010540037 A 12/2010
(Continued)

OTHER PUBLICATIONS

Notification of Transmittal of the International Search Report and the Written Opinion of the International Searching Authority, or the Declaration, dated Mar. 9, 2016, 10 pages.
(Continued)

*Primary Examiner* — Scott M. Getzow
(74) *Attorney, Agent, or Firm* — Seager, Tufte & Wickhem LLP.

(57) ABSTRACT

Devices and circuits for reducing sizes of medical devices are disclosed. In one example, an implantable medical device (IMD) may include a housing, multiple electrodes outside of the housing, an energy storage device within the housing, and a circuit within the housing and connected to the energy storage device and the two or more electrodes. In some cases, the circuit may include two or more island sections, with each island section connected to at least one other island section by a ribbon section. Each island section may have two opposing major surfaces. A first island section and a second island section may be stacked within the housing such that one of the two major surfaces of the first island section faces one of the two opposing major surfaces of the second island section.

1 Claim, 11 Drawing Sheets

(51) Int. Cl.
*A61N 1/05* (2006.01)
*A61N 1/365* (2006.01)
*A61N 1/375* (2006.01)

(56) References Cited

U.S. PATENT DOCUMENTS

| | | | |
|---|---|---|---|
| 6,297,943 | B1 | 10/2001 | Carson |
| 6,307,751 | B1 | 10/2001 | Bodony et al. |
| 6,498,951 | B1 | 12/2002 | Larson et al. |
| 6,539,253 | B2 | 3/2003 | Thompson et al. |
| 6,746,797 | B2 | 6/2004 | Benson et al. |
| 7,211,884 | B1 | 5/2007 | Davis et al. |
| 8,457,744 | B2 | 6/2013 | Janzig et al. |
| 8,525,340 | B2 | 9/2013 | Eckhardt et al. |
| 8,571,678 | B2 | 10/2013 | Wang |
| 2003/0040779 | A1 | 2/2003 | Engmark et al. |
| 2004/0068302 | A1 | 4/2004 | Rodgers et al. |
| 2004/0176818 | A1* | 9/2004 | Wahlstrand .......... A61N 1/3605 607/45 |
| 2005/0288743 | A1 | 12/2005 | Ahn et al. |
| 2006/0042830 | A1* | 3/2006 | Maghribi ................ H05K 1/032 174/256 |
| 2009/0266573 | A1 | 10/2009 | Engmark et al. |
| 2010/0114214 | A1 | 5/2010 | Morelli et al. |
| 2011/0230923 | A1* | 9/2011 | Swanson ................ A61N 1/375 607/5 |
| 2013/0345770 | A1 | 12/2013 | Dianaty et al. |
| 2014/0214104 | A1* | 7/2014 | Greenhut ........... A61N 1/37288 607/4 |
| 2015/0157861 | A1* | 6/2015 | Aghassian ......... A61N 1/36125 607/2 |
| 2016/0220814 | A1* | 8/2016 | Chiao .................. A61N 1/3756 |

FOREIGN PATENT DOCUMENTS

| | | |
|---|---|---|
| JP | 2013540022 A | 10/2013 |
| JP | 2013544598 A | 12/2013 |

OTHER PUBLICATIONS

Office Action for Application No. 2017-529072, 8 pages, dated Jul. 3, 2018.

* cited by examiner

IMPLANTABLE MEDICAL DEVICE WITH STACKED CIRCUIT COMPONENTS

CROSS REFERENCE TO RELATED APPLICATIONS

This application claims the benefit of U.S. Provisional Patent Application Ser. No. 62/086,015 filed on Dec. 1, 2014, the disclosures of each incorporated herein by reference.

TECHNICAL FILED

The present disclosure generally relates to devices and electrical circuits for delivering electrical stimulation therapy to a patient, and more particularly, to devices, and electrical circuits for delivering electrical stimulation therapy to a patient from an implantable medical device.

BACKGROUND

Implantable medical devices are commonly used today to monitor a patient and/or deliver therapy to a patient. For example, implantable sensors are often used to monitor one or more physiological parameters of a patient, such as heart beats, heart sounds, ECG, respiration, etc. In another example, implantable neurostimulators can be used to provide neurostimulation therapy to a patient. In yet another example, pacing devices can be used to treat patients suffering from various heart conditions that may result in a reduced ability of the heart to deliver sufficient amounts of blood to a patient's body. Such heart conditions may lead to rapid, irregular, and/or inefficient heart contractions. To help alleviate some of these conditions, various devices (e.g., pacemakers, defibrillators, etc.) can be implanted in a patient's body. Such devices may monitor and provide electrical stimulation to the heart to help the heart operate in a more normal, efficient and/or safe manner. In some applications, it may be beneficial for the implantable medical devices to have a small form factor or to minimize a volume of the device used for particular components, such as for electrical circuits, to enhance the volume available for an energy storage device such as a battery.

SUMMARY

The present disclosure generally relates to devices and electrical circuits for delivering therapy to a patient, and more particularly, to devices and electrical circuits for delivering therapy to a patient from an implantable medical device. In one example, an implantable medical device (IMD) is configured for implantation within a patient, and may have a hermetically sealed housing, two or more electrodes electrically exposed outside of the housing, an energy storage device disposed within the housing, a circuit disposed within the housing and electrically connected to the energy storage device and the two or more electrodes. In some instances, it may be beneficial for the LCP to have a small form factor and/or to minimize a volume of the device used for particular components, such as for electrical circuits, in order to enhance the volume available for an energy storage device such as a battery. In one example LCP, the circuit may include two or more island sections with each island section electrically connected to at least one other island section by a ribbon section, wherein each island section has two opposing major surfaces. A first one of the two or more island sections and a second one of the two or more island sections may be stacked within the housing such that one of the two major surfaces of the first island section faces one of the two opposing major surfaces of the second island section. Stacking the circuits in this manner may help reduce the volume of the device used for the electrical circuit leaving more room for the energy storage device. While an LCP is used here as an example, it is contemplated that the concepts described herein can be applied to any suitable implantable medical device, as desired.

Alternatively or additionally, in the above example, the two or more island sections and the ribbon section may have may a common substrate.

Alternatively or additionally, in any of the above examples, the circuit may include a flexible circuit.

Alternatively or additionally, in any of the above examples, the two or more island sections may include printed circuit boards.

Alternatively or additionally, in any of the above examples, each of the ribbon sections may include a flexible circuit.

Alternatively or additionally, in any of the above examples, the housing may define an internal housing volume, and the energy storage device may fill at least 70% of the internal housing volume.

Alternatively or additionally, in any of the above examples, the energy storage device may fill at least 80% of the volume of the housing.

Alternatively or additionally, in any of the above examples, the housing may be an elongated housing having a length dimension, and may define a cross-sectional area transverse to the length dimension, and the circuit may fill at least 80% of the cross sectional area.

Alternatively or additionally, in any of the above examples, the two major surfaces of the first island section may extend transverse to the length dimension of the housing, and an area of each of the two major surfaces of the first island section may be at least 80% of the cross sectional area.

Alternatively or additionally, in any of the above examples, the housing may be an elongated housing having a length dimension, and may define a cross-sectional area transverse to the length dimension, and the circuit may fill at least 90% of the cross sectional area.

Alternatively or additionally, in any of the above examples, the IMD may be a leadless cardiac pacemaker, and wherein the circuit may be configured to, via the two or more electrodes, sense intrinsically generated electrical signals and deliver electrical stimulation pulses to the patient.

In another example, an implantable medical device (IMD) configured for implantation within a patient may comprise a hermetically sealed housing, two or more electrodes electrically exposed outside of the housing, an energy storage device disposed within the housing, and a circuit disposed within the housing and electrically connected to the energy storage device and the two or more electrodes. The circuit may comprise two or more island sections with each island section electrically connected to at least one other island section by a ribbon section. Each island section may have two opposing major surfaces, and a first one of the two or more island sections and a second one of the two or more island sections may be stacked within the housing such that one of the two major surfaces of the first island section faces one of the two opposing major surfaces of the second island section.

Alternatively or additionally, in the above example, the two or more island sections and the ribbon section may have a common substrate.

Alternatively or additionally, in any of the above examples, the circuit may comprise a flexible circuit.

Alternatively or additionally, in any of the above examples, the two or more island sections may comprise printed circuit boards.

Alternatively or additionally, in any of the above examples, each of the ribbon sections may comprise a flexible circuit.

Alternatively or additionally, in any of the above examples, the housing may define an internal housing volume, and wherein the energy storage device may fill at least 70% of the internal housing volume.

Alternatively or additionally, in any of the above examples, the energy storage device may fill at least 80% of the volume of the housing.

Alternatively or additionally, in any of the above examples, the housing may be an elongated housing having a length dimension, and may define a cross-sectional area transverse to the length dimension, and the circuit may fill at least 80% of the cross sectional area.

Alternatively or additionally, in any of the above examples, the two major surfaces of the first island section may extend transverse to the length dimension of the housing, and an area of each of the two major surfaces of the first island section may be at least 80% of the cross sectional area.

Alternatively or additionally, in any of the above examples, the housing may be an elongated housing having a length dimension, and may define a cross-sectional area transverse to the length dimension, and the circuit may fill at least 90% of the cross sectional area.

Alternatively or additionally, in any of the above examples, each ribbon section may be more flexible than the island sections.

Alternatively or additionally, in any of the above examples, the circuit may comprise three island sections with a first island section connected to a second island section with a first ribbon section, and the second island section connected to a third island section with a second ribbon section, wherein the first island section, the second island section and the third island section may be stacked within the housing with the first island section positioned between the second island section and the third island section.

Alternatively or additionally, in any of the above examples, the circuit may comprise three island sections with a first island section connected to a second island section with a first ribbon section, and the second island section connected to a third island section with a second ribbon section, wherein the first island section, the second island section and the third island section may be stacked within the housing, with the second island section positioned between the first island section and the third island section.

Alternatively or additionally, in any of the above examples, one or more circuit components may be connected to at least two of the two or more island sections.

Alternatively or additionally, in any of the above examples, each ribbon section may comprise a metal portion bonded between two polymer portions, and each of the island sections may comprise a first metal portion bonded between two polymer portions, and second metal portions bonded to the two polymer portions.

Alternatively or additionally, in any of the above examples the IMD may be a leadless cardiac pacemaker, and wherein the circuit may be configured to, via the two or more electrodes, sense intrinsically generated electrical signals and deliver electrical stimulation pulses to the patient.

In another example, an implantable medical device (IMD) configured for implantation within a patient may include an elongated housing having a major and minor dimension, two or more electrodes electrically exposed outside of the housing, an energy storage device disposed within the housing, and a flexible circuit disposed within the housing and electrically connected to the energy storage module and the two or more electrodes. The flexible circuit may include a flexible substrate that has two or more island sections and one or more ribbon sections, wherein each island section is electrically connected to at least one other island section by one or more ribbon section. Each island section may have two opposing major surfaces. In one example, a first one of the two or more island sections and a second one of the two or more island sections may be stacked within the housing such that the two opposing major surfaces of the first one of the two or more island sections and the two opposing major surfaces of the second one of the two or more island sections extend transverse to the major dimension of the elongated housing. In some cases, the first one of the two or more island sections and the second one of the two or more island sections may be positioned within the elongated housing laterally adjacent to the energy storage device.

Alternatively or additionally, in any of the above examples, each ribbon section may be more flexible than the island sections.

Alternatively or additionally, in any of the above examples, the flexible circuit may include three island sections, wherein the first island section is connected to the second island section with a first ribbon section, and the second island section is connected to the third island section with a second ribbon section.

Alternatively or additionally, in any of the above examples, the first island section, the second island section and the third island section may be stacked within the housing, with the first island section positioned between the second island section and the third island section.

Alternatively or additionally, in any of the above examples, the first island section, the second island section and the third island section may be stacked within the housing, with the second island section positioned between the first island section and the third island section.

Alternatively or additionally, in any of the above examples, the elongated housing may define an internal housing volume, and wherein the energy storage device may fill at least 80% of the internal housing volume.

Alternatively or additionally, in any of the above examples, one or more circuit components may be connected to at least two of the two or more island sections.

Alternatively or additionally, in any of the above examples, each ribbon section may include a metal portion bonded between two polymer portions, and each of the island sections may include a first metal portion bonded between two polymer portions, and second metal portions bonded to the two polymer portions.

In another example, a flexible circuit for controlling delivery of electrical stimulation pulses to tissue of a patient may include a flexible substrate, wherein the flexible substrate has two or more island sections with each island section electrically connected to at least one other island section by a ribbon section. The two or more island sections and the ribbon section may have a common substrate. In some instances, an application specific integrated circuit (ASIC) may be mounted on one of the island sections, wherein the ASIC is configured to control delivery of electrical stimulation to tissue of a patient. In some cases, each ribbon section may be configured to bend to allow the two or more island sections to be positioned in a substantially parallel stacked relationship.

Alternatively or additionally, in any of the above examples, the flexible circuit may further include one or more electrical components mounted on another one of the island sections that does not have the ASIC.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which.

Figure 1:
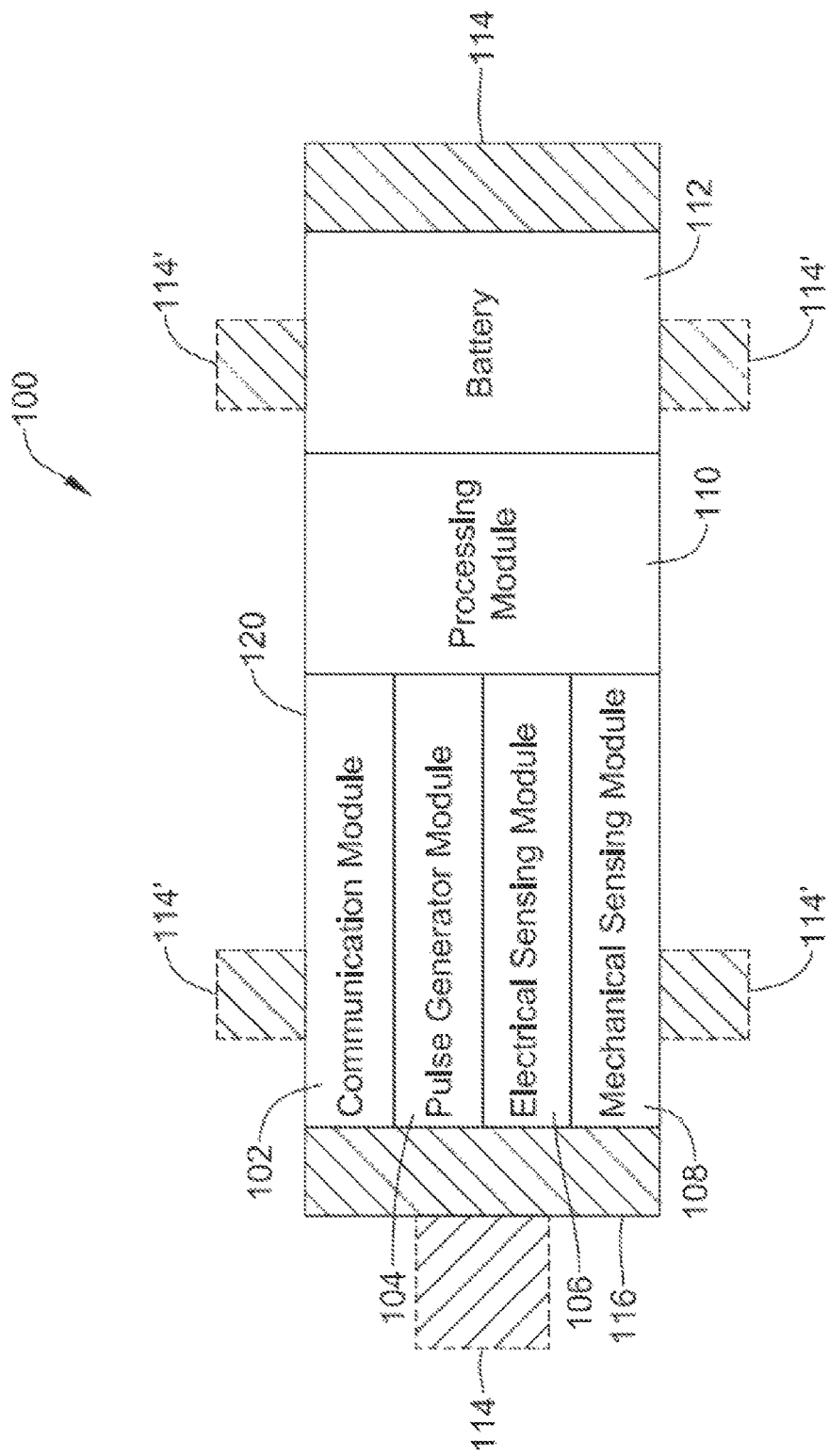
FIG. 1 is a schematic block diagram of an illustrative leadless cardiac pacemaker (LCP) according to one example of the present disclosure.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

FIG. 1 is a conceptual drawing of an exemplary leadless cardiac pacemaker (LCP) that may be implanted into a patient and may operate to sense physiological signals and parameters and deliver one or more types of electrical stimulation therapy to tissues of the patient. Example electrical stimulation therapy includes anti-tachycardia pacing (ATP) therapy, cardiac resynchronization therapy (CRT), bradycardia therapy, various types of pacing therapy including rate responsive pacing therapy, and/or the like. As can be seen in FIG. 1, LCP 100 may be a compact device with all components housed within LCP 100 or directly on housing 120. LCP 100 may include communication module 102, pulse generator module 104, electrical sensing module 106, mechanical sensing module 108, processing module 110, energy storage module 112, and electrodes 114.

As depicted in FIG. 1, LCP 100 may include electrodes 114, which can be secured relative to housing 120 but exposed to the tissue and/or blood surrounding LCP 100. Electrodes 114 may generally conduct electrical signals to and from LCP 100 and the surrounding tissue and/or blood. Such electrical signals can include communication pulses, electrical stimulation pulses, and intrinsic cardiac electrical signals. Intrinsic cardiac electrical signals may consist of the electrical signals generated by the heart and may be represented by an electrocardiogram (ECG). Electrodes 114 can be made up of one or more biocompatible conductive materials such as various metals or alloys that are known to be safe for implantation within a human body. In some instances, electrodes 114 may be generally disposed on either end of LCP 100 and may be in electrical communication with one or more of modules 102, 104, 106, 108, and 110. In examples where electrodes 114 are secured directly to housing 120, electrodes 114 may have an insulative portion that electrically isolates electrodes 114 from adjacent electrodes, housing 120, and/or other portions of LCP 100. Some or all of electrodes 114 may be spaced from housing 120 and connected to housing 120 and/or other components of LCP 100 through connecting wires. In such embodiments, the electrodes 114 may be placed on a on a tail that extends from the housing 120. As shown in FIG. 1, in some examples, LCP 100 may additionally include electrodes 114'. Electrodes 114' are similar to electrodes 114 except that electrodes 114' are disposed on the sides of LCP 100 and increase the number of electrodes by which LCP 100 may deliver communication pulses and electrical stimulation pulses and/or sense for intrinsic cardiac electrical signals, communication pulses, and/or electrical stimulation pulses.

Electrodes 114 and/or 114' may have any of a variety of sizes and/or shapes, and may be spaced at any of a variety of distances. For example, electrodes 114 may have a diameter of two to twenty millimeters (mm). However, in other examples, electrodes 114 and/or 114' may have a diameter of two, three, five, seven millimeters (mm), or any other suitable diameter, dimension and shape. Example lengths for electrodes 114 and/or 114' include a length of zero, one, three, five, ten millimeters (mm), or any other suitable length. As used herein, the length is a dimension of electrodes 114 and/or 114' that extends outward from housing 120. Additionally, at least some of electrodes 114 and/or 114' may be spaced from one another by a distance of twenty, thirty, forty, fifty millimeters (mm), or any other suitable distance. The electrodes 114 and/or 114' of a single device may have different sizes with respect to each other, and the spacing of the electrodes on the device may not be uniform.

Communication module 102 may be electrically coupled to electrodes 114 and/or 114' and configured to deliver communication pulses to tissues of the patient for communicating with other devices such as sensors, programmers, other medical devices, and the like. Communication pulses, as used herein, may be any modulated signal that conveys information to another device, either by itself or in conjunction with one or more other modulated signals. In some examples, communication pulses are limited to only including sub-threshold signals which convey information. Other devices that communication module 102 may be configured to communicate with may be located either external or internal to the patient's body. Communication module 102 may additionally be configured to sense for communication pulses delivered by the other devices, which are located externally to LCP 100. Irrespective of the location, LCP and the other devices may communicate with each other via communication module 102 to accomplish one or more desired functions. Some example functions include storing communicated data, using communicated data for determining occurrences of arrhythmias, coordinating delivery of electrical stimulation therapy, and/or other functions.

LCP 100 and the other devices may use the delivered communication pulses to communicate raw information, processed information, messages, and/or other data. Raw information may include information such as sensed electrical signals (e.g. a sensed ECG), signals gathered from coupled sensors, and the like. In some examples, the raw information may include signals that have been filtered using one or more signal processing techniques. Processed information may include any information that has been determined by LCP 100. For example, processed information may include a determined heart rate, timings of determined heartbeats, timings of other determined events, determinations of threshold crossings, expirations of monitored time periods, and determined parameters such as activity parameters, blood-oxygen parameters, blood pressure parameters, heart sound parameters, and the like. Messages may include instructions directing another device to take action, notifications of imminent actions of the sending device, requests for reading from the receiving device or writing data to the receiving device.

In at least some examples, communication module 102 (or LCP 100) may further include switching circuitry to selectively connect one or more of electrodes 114 and/or 114' to communication module 102 in order to select via which electrodes 114 and/or 114' communication module 102 delivers the communication pulses. Additionally, communication module 102 may be configured to use one or more methods for communicating with other devices. For example, communication module 102 may communicate via conducted signals, radiofrequency (RF) signals, optical signals, acoustic signals, inductive coupling, and/or any other signals or methods suitable for communication.

Pulse generator module 104 of LCP 100 may also be electrically connected to one or more of electrodes 114 and/or 114'. Pulse generator module 104 may be configured to generate electrical stimulation pulses and deliver the electrical stimulation pulses to tissues of a patient via electrodes 114 and/or 114' electrodes in order to effectuate one or more electrical stimulation therapies. Electrical stimulation pulses as used herein are meant to encompass any electrical signals that may be delivered to tissue of a patient for purposes of treatment of any type of disease or abnormality. When used to treat heart diseases or abnormalities, the electrical stimulation pulses may generally be configured so as to capture the heart of the patient—cause the heart to contract in response to the delivered electrical stimulation pulse. In at least examples where pulse generator 104 is configured to generate specific types of electrical stimulation pulses termed defibrillation/cardioversion pulses, pulse generator module 104 may include one or more capacitor elements.

Pulse generator module 104 may include capability to modify the electrical stimulation pulses, such as by adjusting a pulse width or amplitude of the electrical stimulation pulses, in order to ensure that the delivered electrical stimulation pulses consistently capture the heart. Pulse generator module 104 may use energy stored in energy storage module 112 to generate the electrical stimulation pulses. In at least some examples, pulse generator module 104 (or LCP 100) may further include switching circuitry to selectively connect one or more of electrodes 114 and/or 114' to pulse generator module 104 in order to select via which electrodes 114 and/or 114' pulse generator 104 delivers the electrical stimulation pulses.

In some examples, LCP 100 may include electrical sensing module 106 and mechanical sensing module 108. Electrical sensing module 106 may be configured to sense intrinsic cardiac electrical signals conducted from electrodes 114 and/or 114' to electrical sensing module 106. For example, electrical sensing module 106 may be electrically connected to one or more electrodes 114 and/or 114' and electrical sensing module 106 may be configured to receive cardiac electrical signals conducted through electrodes 114 and/or 114'. In some examples, the cardiac electrical signals may represent local information from the chamber in which LCP 100 is implanted. For instance, if LCP 100 is implanted within a ventricle of the heart, cardiac electrical signals sensed by LCP 100 through electrodes 114 and/or 114' may represent ventricular cardiac electrical signals. Mechanical sensing module 108 may include, or be electrically connected to, various sensors, such as accelerometers, blood pressure sensors, heart sound sensors, blood-oxygen sensors, and/or other sensors which measure one or more physiological parameters of the heart and/or patient. Mechanical sensing module 108 may gather signals from the sensors indicative of the various physiological parameters. Both electrical sensing module 106 and mechanical sensing module 108 may be further connected to processing module 110 and may provide signals representative of the sensed cardiac electrical signals and/or physiological signals to processing module 110. Although described with respect to FIG. 1 as separate sensing modules, in some examples, electrical sensing module 106 and mechanical sensing module 108 may be combined into a single module.

Processing module 110 may be configured to control the operation of LCP 100. For example, processing module 110 may be configured to receive cardiac electrical signals from electrical sensing module 106 and/or physiological signals from mechanical sensing module 108. Based on the received signals, processing module 110 may determine occurrences and types of arrhythmias. Processing module 110 may further receive information from communication module 102. In some examples, processing module 110 may additionally use such received information to determine occurrences and types of arrhythmias. However, in other examples, LCP 100 may use the received information instead of the signals received from electrical sensing module 106 and/or mechanical sensing module 108—for instance if the received information is more accurate than the signals received from electrical sensing module 106 and/or mechanical sensing module 108 or if electrical sensing module 106 and/or mechanical sensing module 108 have been disabled or omitted from LCP 100.

Based on any determined arrhythmias, processing module 110 may then control pulse generator module 104 to generate electrical stimulation pulses in accordance with one or more electrical stimulation therapies to treat the determined arrhythmias. For example, processing module 110 may control pulse generator module 104 to generate pacing pulses with varying parameters and in different sequences to effectuate one or more electrical stimulation therapies. In controlling pulse generator module 104 to deliver bradycardia pacing therapy, processing module 110 may control pulse generator module 104 to deliver pacing pulses designed to capture the heart of the patient at a regular interval to prevent the heart of a patient from falling below a predetermined threshold. For ATP therapy, processing module 110 may control pulse generator module 104 to deliver pacing pulses at a rate faster than an intrinsic heart rate of a patient in attempt to force the heart to beat in response to the delivered pacing pulses rather than in response to intrinsic cardiac electrical signals. Processing module 110 may then control pulse generator module 104 to reduce the rate of delivered pacing pulses down to a safe level. In CRT, processing module 110 may control pulse generator module 104 to deliver pacing pulses in coordination with another device to cause the heart to contract more efficiently. Additionally, in cases where pulse generator module 104 is capable of generating defibrillation and/or cardioversion pulses for defibrillation/cardioversion therapy, processing module 110 may control pulse generator module 104 to generate such defibrillation and/or cardioversion pulses. In other examples, processing module 110 may control pulse generator module 104 to generate electrical stimulation pulses to provide electrical stimulation therapies different than those described herein to treat one or more detected cardiac arrhythmias.

Aside from controlling pulse generator module 104 to generate different types of electrical stimulation pulses and in different sequences, in some examples, processing module 110 may also control pulse generator module 104 to generate the various electrical stimulation pulses with varying pulse parameters. For example, each electrical stimulation pulse may have a pulse width and a pulse amplitude. Processing module 110 may control pulse generator module 104 to generate the various electrical stimulation pulses with specific pulse widths and pulse amplitudes. For example, processing module 110 may cause pulse generator module 104 to adjust the pulse width and/or the pulse amplitude of electrical stimulation pulses if the electrical stimulation pulses are not effectively capturing the heart. Such control of the specific parameters of the various electrical stimulation pulses may ensure that LCP 100 is able to provide effective delivery of electrical stimulation therapy.

In some examples, processing module 110 may further control communication module 102 to send information to other devices. For example, processing module 110 may control communication module 102 to generate one or more communication pulses for communicating with other devices of a system of devices. For instance, processing module 110 may control communication module 102 to generate communication pulses in particular sequences, where the specific sequences convey different data to other devices. Communication module 102 may also conduct any received communication signals to processing module 110 for potential action by processing module 110.

In further examples, processing module 110 may additionally control switching circuitry by which communication module 102 and pulse generator module 104 deliver communication pulses and electrical stimulation pulses to tissue of the patient. As described above, both communication module 102 and pulse generator module 104 may include circuitry for connecting one or more electrodes 114 and/114' to communication module 102 and pulse generator module 104 so those modules may deliver the communication pulses and electrical stimulation pulses to tissue of the patient. The specific combination of one or more electrodes by which communication module 102 and pulse generator module 104 deliver communication pulses and electrical stimulation pulses influence the reception of communication pulses and/or the effectiveness of electrical stimulation pulses. Although it was described that each of communication module 102 and pulse generator module 104 may include switching circuitry, in some examples LCP 100 may have a single switching module connected to all of communication module 102, pulse generator module 104, and electrodes 114 and/or 114'. In such examples, processing module 110 may control the single switching module to connect modules 102/104 and electrodes 114/114'.

In still additional examples, processing module 110 may control pulse generator module 104 to generate the communication pulses for communicating with external devices. In such examples, communication module 102 may not include the capability to generate communication pulses. In some even additional examples, electrical sensing module 106 may further include the capability to sense communication pulses. In such examples, electrical sensing module 106 may communicate any received communication pulses to processing module 110. In such examples, LCP 100 may not include communication module 102, as the functions of communication module 102 are subsumed within pulse generator module 104 and electrical sensing module 106. However, in such examples, LCP 100 may not be able to simultaneously generate both communication pulses and electrical stimulation pulses.

In some examples, processing module 110 may include a pre-programmed chip, such as a very-large-scale integration (VLSI) chip or an application specific integrated circuit (ASIC). In such embodiments, the chip may be pre-programmed with control logic in order to control the operation of LCP 100. By using a pre-programmed chip, processing module 110 may use less power than other programmable circuits while able to maintain basic functionality, thereby increasing the battery life of LCP 100. In other examples, processing module 110 may include a programmable microprocessor or the like. Such a programmable microprocessor may allow a user to adjust the control logic of LCP 100 after manufacture, thereby allowing for greater flexibility of LCP 100 than when using a pre-programmed chip.

Processing module 110, in additional examples, may further include a memory circuit and processing module 110 may store information on and read information from the memory circuit. In other examples, LCP 100 may include a separate memory circuit (not shown) that is in communication with processing module 110, such that processing module 110 may read and write information to and from the separate memory circuit. The memory circuit, whether part of processing module 110 or separate from processing module 110 may have address lengths of, for example, eight bits. However, in other examples, the memory circuit may have address lengths of sixteen, thirty-two, or sixty-four bits, or any other bit length that is suitable. Additionally, the memory circuit may be volatile memory, non-volatile memory, or a combination of both volatile memory and non-volatile memory.

Energy storage module 112 may provide a power source to LCP 100 for its operations. In some examples, energy storage module 112 may be a non-rechargeable lithium-based battery. In other examples, the non-rechargeable battery may be made from other suitable materials known in the art. Because LCP 100 is an implantable device, access to LCP 100 may be limited. In such circumstances, it is necessary to have sufficient energy capacity to deliver therapy over an extended period of treatment such as days, weeks, months, or years. In some examples, energy storage module 112 may a rechargeable battery in order to facilitate increasing the useable lifespan of LCP 100. In still other examples, energy storage module 112 may be other types of energy storage devices such as capacitors.

To implant LCP 100 inside a patient's body, an operator (e.g., a physician, clinician, etc.), may fix LCP 100 to the cardiac tissue of the patient's heart. To facilitate fixation, LCP 100 may include one or more anchors 116. Anchor 116 may include any number of fixation or anchoring mechanisms. For example, anchor 116 may include one or more pins, staples, threads, screws, helix, tines, and/or the like. In some examples, although not shown, anchor 116 may include threads on its external surface that may run along at least a partial length of anchor 116. The threads may provide friction between the cardiac tissue and the anchor to help fix anchor 116 within the cardiac tissue. In other examples, anchor 116 may include other structures such as barbs, spikes, or the like to facilitate engagement with the surrounding cardiac tissue.

Figure 2:
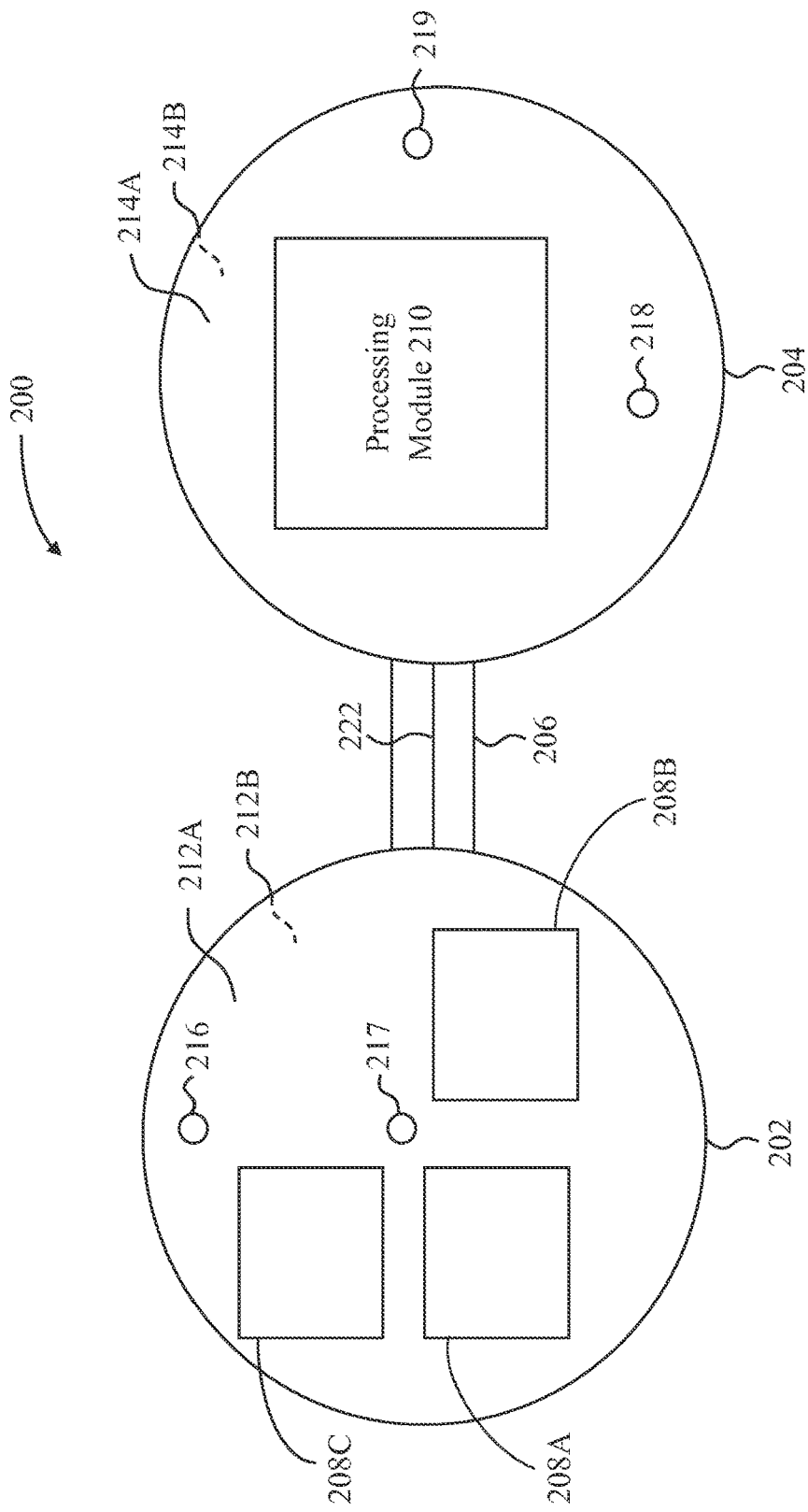
FIG. 2 is a schematic of an example electrical circuit that may implement various functions of an implantable medical device, in accordance with aspects of the present disclosure.

FIG. 2 depicts an example electrical circuit that may implement the functions described with respect to communication module 102, pulse generator module 104, electrical sensing module 106, mechanical sensing module 108, and/or processing module 110, in accordance with aspects of the present disclosure. Specifically, FIG. 2 depicts example electrical circuit 200. Electrical circuit 200 may include island sections 202, 204 connected by ribbon section 206. Each of island sections 202, 204 may have first major opposing surfaces 212A, 214A, and second major opposing surfaces 212B, 214B, respectively. FIG. 2 additionally depicts processing module 210 fixed to island section 204 and circuit elements 208A, 208B, and 208C fixed to island section 202. In one example, processing module 210 and circuit elements 208A, 208B, and 208C may represent circuit elements that implement the functions of communication module 102, pulse generator module 104, electrical sensing module 106, mechanical sensing module 108, and/or processing module 110. Processing module 210 may include any of the circuit elements or components described with respect to processing module 110, such as a pre-programmed logic chip or a programmable microprocessor. Circuit elements 208A, 208B, and 208C may represent capacitors, resistors, diodes, or other circuit elements. Additionally, although circuit elements 208A, 208B, and 208C and processing module are all depicted on first major opposing surfaces 212A, 214A of island sections 202, 204, in other examples some or all of the components may be attached to second major opposing surfaces 212B, 214B. In still other examples, island sections 202 and/or 204 may have one or more components attached to both major opposing surfaces.

In the example shown, island sections 202, 204 additionally include feedthroughs 216, 217, 218, and 219. When inserted into an implantable medical device, such as LCP 100, each of feedthroughs 216, 217, 218, and 219 may be electrically connected to electrodes 114/114', an electrical common reference, and/or an energy storage device. Additionally, ribbon section 206 may include trace 222. Trace(s) 222 may be electrically conductive, thereby providing one or more electrical traces (i.e. connections) between island 202 and island 204.

In some examples, each island section 202, 204 may be circular in shape, as illustrated in FIG. 2, but this is not required. Each island section 202, 204 may have a diameter that is slightly less than an inner diameter of a cross section of an implantable medical device housing (e.g. LCP 100) so that island sections 202, 204 may fit within the device when stacked. Some example diameters include 3.80 millimeters to 12.7 millimeters. However, in other examples, islands 202, 204 may be triangular, square, ovular, or any other suitable shape. In at least some examples, the specific shape of islands sections 202, 204 may generally match a cross section shape of an implantable medical device. Some example ranges for the length of ribbon section 206 include 3.80 millimeters to 12.7 millimeters.

Island sections 202, 204 may include rigid printed circuit boards (PCBs). In such cases, island sections 202, 204 may include metal or other traces electrically connecting each of the components on each of islands 202, 204 and trace(s) 222 of ribbon section 206. Ribbon section 206, on the other hand, may include a flexible substrate, for example a polymer including polyamide or any other suitable flexible substrate. Trace(s) 222 may be embedded within the polymer of ribbon section 206 and may be electrically insulated from the environment external to electrical circuit 200. Generally, ribbon section 206 may be relatively more flexible than island sections 202, 204. Accordingly, when disposed within an implantable medical device, such as LCP 100, ribbon section 206 may be folded or bent to allow island sections 202, 204 to be stacked relative to one another without bending the island sections 202, 204 to a significant degree (e.g. less than a 15 degree deflection between two tangent lines, where each tangent line is tangent to the upper surface of the island section at a corresponding edge of the island section).

Figure 3:
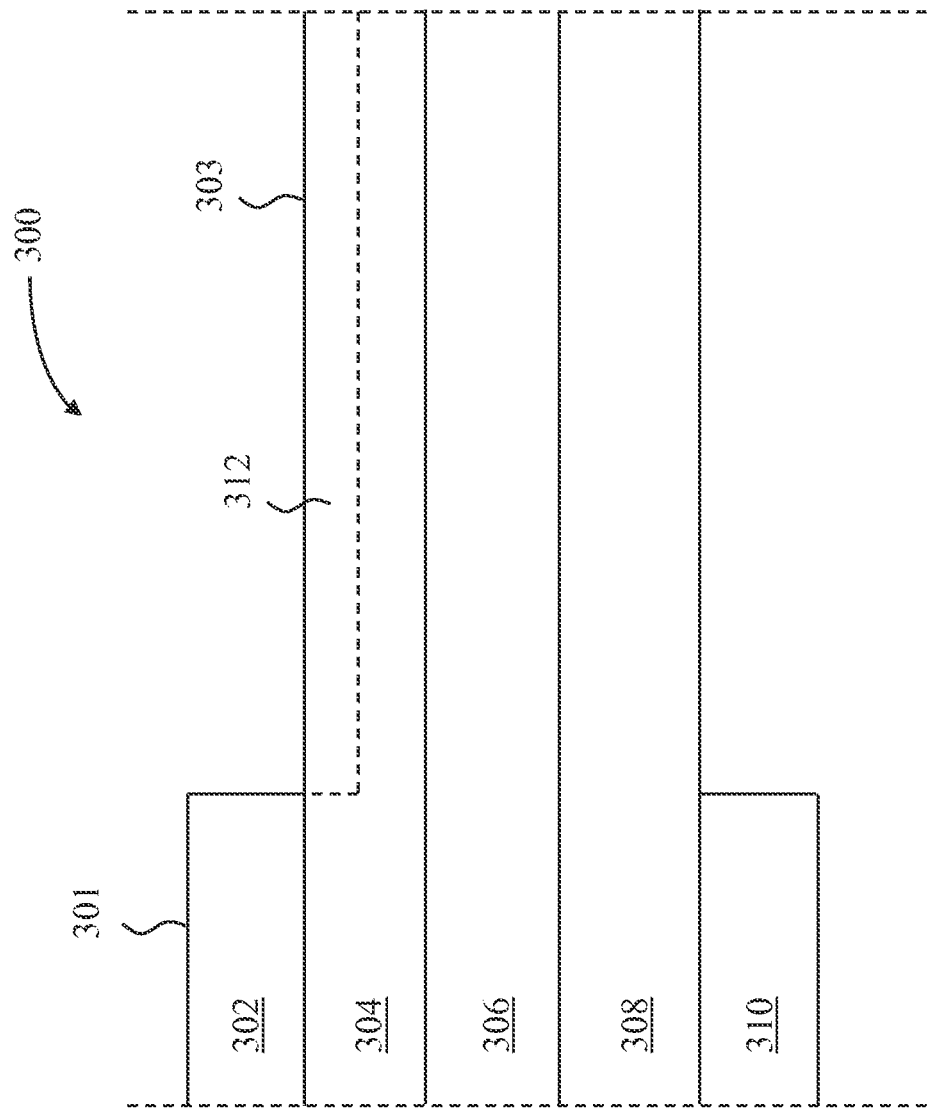
FIG. 3 is an illustration of partial profiles of an example circuit of an implantable medical device, in accordance with aspects of the present disclosure.

In other examples, rather than island sections 202, 204 including rigid PCBs and ribbon section 206 including a flexible substrate, island sections 202, 204 and ribbon section 206 may have a common substrate. FIG. 3 depicts partial profiles of an example circuit where the various parts of the example circuit all have a common substrate. Specifically, FIG. 3 depicts a partial profile of island section 301 and ribbon section 303. Island section 301 may include a multi-layered substrate. Specifically, the multi-layered substrate may include alternating conductive substrates and non-conductive substrates. In at least some examples, the conductive substrate may be metal, or other suitable conductive material, and the non-conductive substrate may be a type of polymer, such as a polyamide or other suitable non-conductive material.

As depicted in FIG. 3, island section 301 may include non-conductive substrates 304 and 308 sandwiched between conductive substrates 302, 306, and 310. In some additional examples, conductive substrate 306 may include specifically patterned traces with non-conductive substrates filling in the spaces between the patterned traces. In such examples, when attached to island section 301, circuit components, such as circuit components 208A, 208B, 208C and/or processing module 210 of FIG. 2, may be electrically connected to conductive substrate 306. In this manner, conductive substrate 306 may create specific conductive pathways (e.g. traces) between the one or more circuit components. Also in some examples, conductive substrate 302 and/or conductive substrate 310 may be electrically isolated from any attached circuit components. In such examples, conductive substrate 302 and/or conductive substrate 310 may act as electromagnetic shields, attenuating or blocking electromagnetic interference.

As seen in FIG. 3, non-conductive substrates 304 and 308 and conductive substrate 306 may run through both island section 301 and ribbon section 301. The addition of conductive substrate 302 and conductive substrate 310 to island section 301 may increase the difference in relative flexibility of island section 301 and ribbon section 303 by making island section 301 more rigid. Additionally, in some examples, a portion of non-conductive substrate 304, such as portion 312, may be removed from ribbon section 303 relative to island section 301. Removal of portion 312 may also increase the difference in relative flexibility of island section 301 and ribbon section 303 by making ribbon section 303 more flexible. Of course, in other examples, a portion of non-conductive substrate 308 in ribbon section 303, or portions from both non-conductive substrate 304 and non-conductive substrate 308, may be removed to increase the difference in relative flexibility between island section 301 and ribbon section 303. The attachment of circuit components, such as circuit components 208A, 208B, 208C, and/or processing module 210, to island section 301 may further increase the difference in relative flexibility between island section 301 and ribbon section 303 by enhancing the rigidity of island section 301.

In some examples, conductive substrates 302 and 306 and non-conductive substrate 304 may be manufactured as an integral composite substrate. In such examples, non-conductive substrate 308 and conductive substrate 310 may be glued to the integral composite substrate of conductive substrates 302 and 306 and non-conductive substrate 304. Additionally in such examples, conductive substrate 301 may be removed along ribbon section 303. In generally, each section of substrate may be relatively thin, thereby allowing circuit 300 to be relatively thin as well. Example thicknesses for conductive substrate 302 and/or conductive substrate 310 range from fifteen to thirty micrometers, and in some examples the thicknesses are twenty-two micrometers. Example thicknesses for non-conductive substrates 304, 308 range from twenty to thirty-five micrometers, and in some examples the thicknesses are twenty-five micrometers. Example thicknesses for conductive substrate 306 range from ten to twenty-five micrometers, and in some examples the thickness is eighteen micrometers. In examples where non-conductive substrate 308 and conductive substrate 310 are glued to the integral composite substrate of conductive substrates 302 and 306 and non-conductive substrate 304, the thickness of the adhesive may range from fifteen to thirty-five micrometers, and in some examples the thickness is twenty-five micrometers. Accordingly, the overall thickness of island section 301 may range from ninety-five micrometers to one-hundred ninety micrometers, and in some examples the thickness may be one-hundred thirty-seven micrometers.

Figure 4:
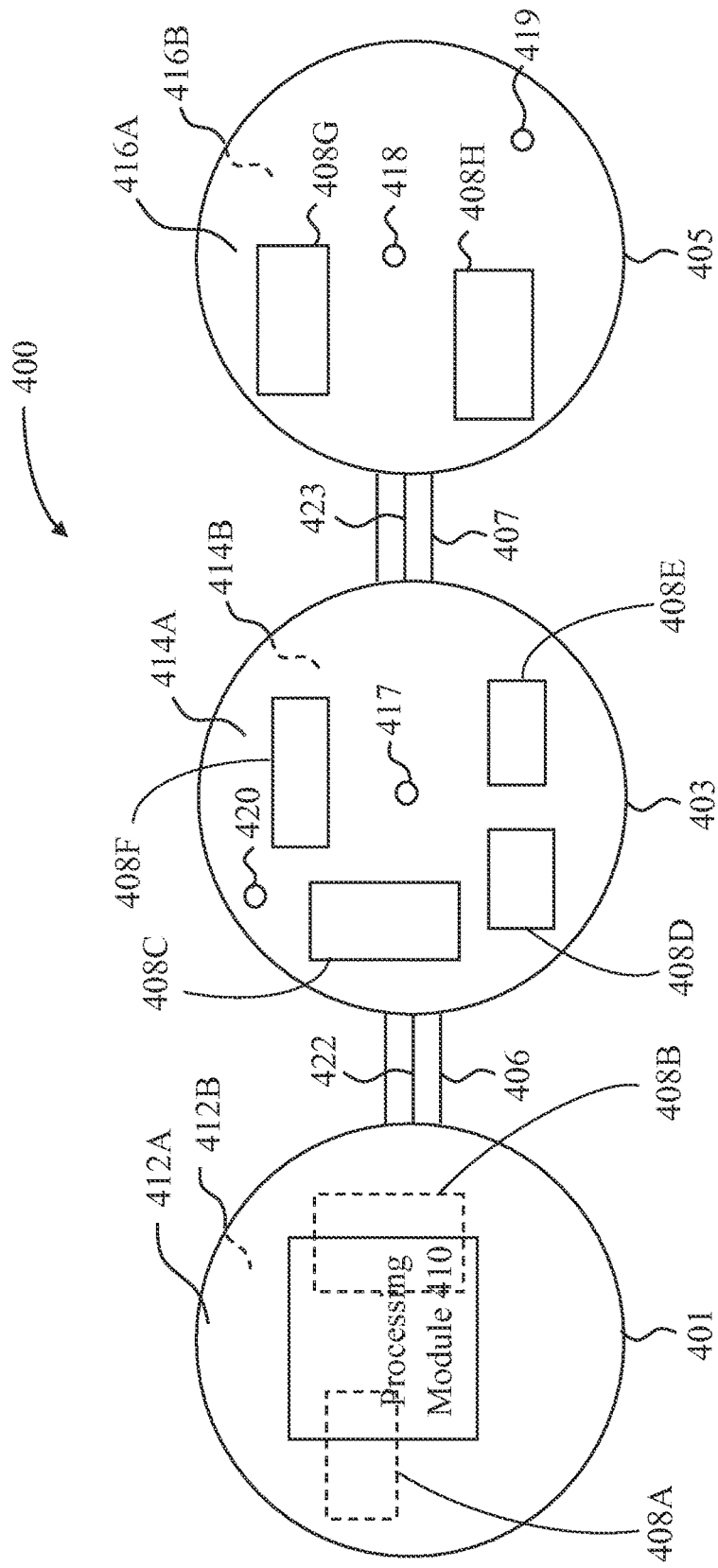
FIG. 4 is another schematic of an example electrical circuit that may implement various functions of an implantable medical device, in accordance with aspects of the present disclosure.

FIG. 4 illustrates another example circuit in accordance with aspects of the present disclosure. In the example of FIG. 4, example circuit 400 has three separate island sections including first island section 401, second island section 403, and third island section 405. Island sections 401, 403, and 405 are shown separated by first ribbon section 406 and second ribbon section 407. As with island sections 202, 204 of FIG. 2, each of island sections 401, 403, and 405 may include first major opposing surfaces 412A, 414A, and 416A and second major opposing surfaces 412B, 414B, and 416B. Second island section 403 and third island section 405 may also include feedthroughs 417, 418, 419, and 420. When circuit 400 is disposed within an implantable medical device, such as LCP 100, feedthroughs 417, 418, 419, and 420 may be electrically connected to electrodes 114/114', an electrical common reference, and/or an energy storage device.

Processing module 410 and circuit elements 408A-H may be examples of circuit elements that may implement the functions of communication module 102, pulse generator module 104, electrical sensing module 106, mechanical sensing module 108, and/or processing module 110. Processing module 410 may include any of the circuit elements or components described with respect to processing module 110, such as a pre-programmed logic chip or a programmable microprocessor. Circuit elements 408A-H may represent capacitors, resistors, diodes, or any other suitable circuit elements.

In some examples, at least one island section may have one or more components affixed to both major opposing surfaces of that island section. In the specific example of FIG. 4, island section 401 includes processing module 410 affixed to first major opposing surface 412A and circuit elements 408A-B (shown in dashed) on second major opposing surface 412B. Generally, island sections 401, 403, and 405 may be similar to island sections 202, 204. For instance, island sections 401, 403, and 405 may have similar shapes and sizes as described with respect to island sections 202, 204 of FIG. 2. Additionally, in examples where island sections 401, 403, and 405 include PCBs, the PCBs may include conductive traces that electrically connect processing module 410 and circuit elements 408A-H to produce the desired circuit functionality. Alternatively, in examples where circuit 400 includes one common substrate, any processing module 410 and/or circuit element 408A-H connected to an island section may be connected to one or more internal conductive trace layers, thereby electrically connecting the processing module 410 and/or the various circuit elements 408A-H to produce the desired circuit functionality.

As with ribbon section 206, ribbon sections 406, 407 may include traces, such as trace 422 in first ribbon section 406 and trace 423 in second ribbon section 407. Traces 422, 423 may be conductive and thereby electrically connect certain components on island sections 401, 403, and 405. Also as with ribbon section 206, first and second ribbon sections 406, 407 may be relatively more flexible than island sections 401, 403, and 405. For example, first and second ribbon sections 406, 407 may be made from a flexible substrate, such as a polymer, with traces 422, 423 embedded within the flexible substrate while island sections 401, 403, and 405 include more rigid PCBs. Alternatively, where island sections 401, 403, and 405 and first and second ribbon sections 406, 407 share a common substrate, first and second ribbon sections 406, 407 may be relatively thinner than island sections 401, 403, and 405. For instance, island sections 401, 403, and 405 and first and second ribbon sections 406, 407 may generally include an internal structure similar to that depicted in FIG. 3.

Additionally, in at least some examples, first ribbon section 406 and second ribbon section 407 may have differing lengths. As depicted in FIG. 4, first ribbon section 406 has a shorter length than second ribbon section 407, however, in other examples, the lengths may be reversed and, of course, the lengths may be the same. The particular relative lengths of first ribbon section 406 and second ribbon section 407 may allow for different stacking configurations, such as described below with respect to FIGS. 6A-C.

Figure 5A:
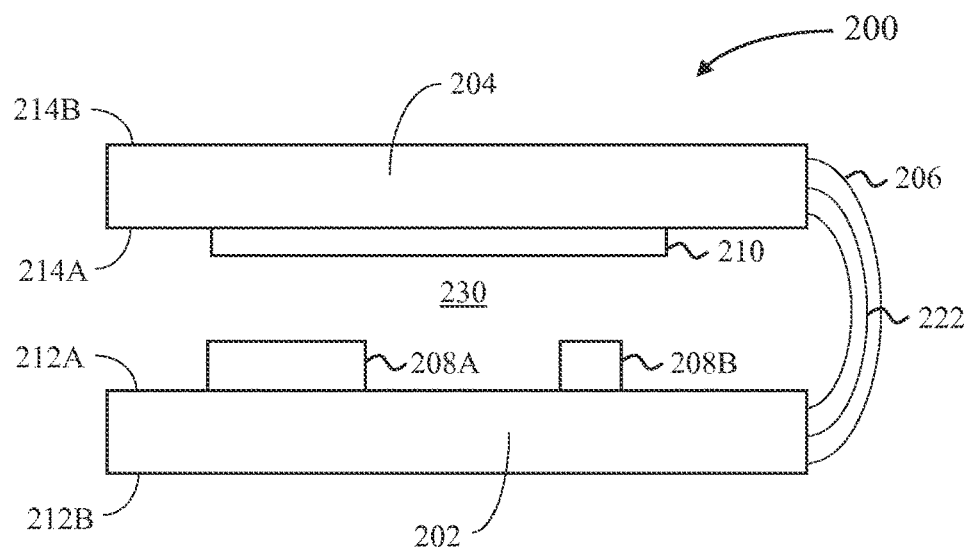
FIGS. 5A-B are example diagrams of orientations of an example electrical circuit, in accordance with aspects of the present disclosure.
Figure 5B:
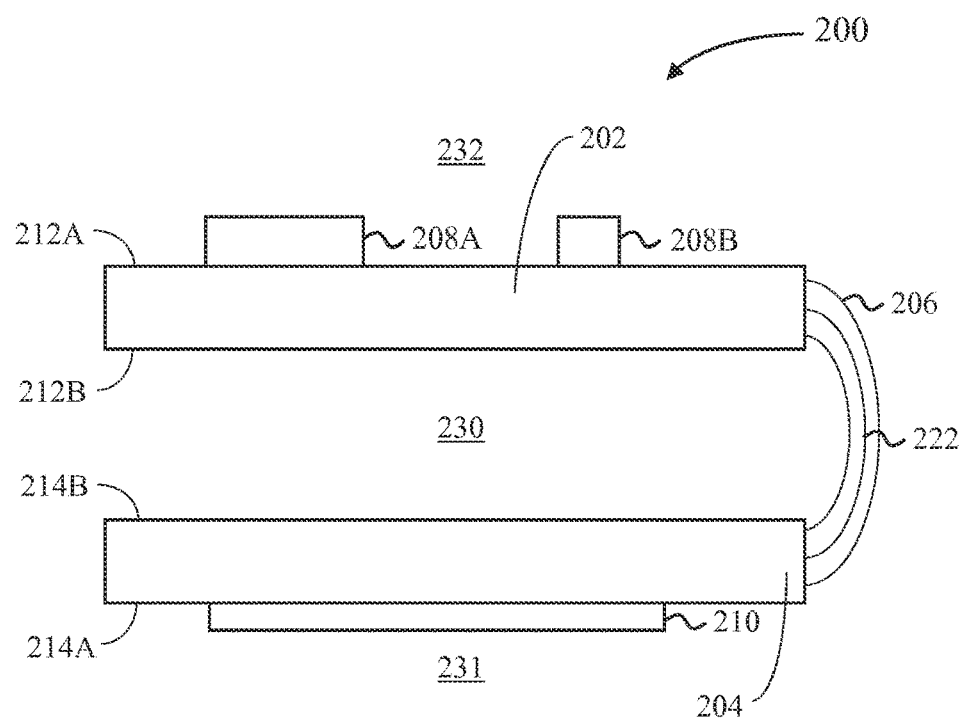

In some examples, the relative flexibility difference between the island sections and the ribbon sections described with respect to FIG. 2-4 may allow the island sections to be stacked on top of one another when disposed within an implantable medical device. FIGS. 5A-B illustrate a couple of example configurations that circuit 200 may take when disposed within an implantable medical device, such as LCP 100. In FIG. 5A, island sections 202 and 204 are stacked with first major opposing surfaces 212A, 214A facing each other. With processing module 210 and circuit elements 208A-C in the configuration as depicted in FIG. 2, this means that processing module 210 and circuit elements 208A-C (circuit element 208C not shown as circuit element 208A may cover up circuit element 208C in the perspective of FIG. 5A) oppose each other with space 230 interposed between the components. In some examples, a filler material may be disposed within space 230 in order to maintain isolation between the components. In at least some examples, the filler material may be formed such that when the filler material is disposed within space 230, the filler material folds around the components to isolate even the components on the same island section. In some examples, the isolation that the filler material provides may be electrical isolation. For instance, the filler material may prevent the components of islands 202 and 204 from contacting each other and causing a short circuit. In other examples, the filler material may instead, or additionally, provide mechanical isolation between the components of islands 202 and 204. For instance, the device housing islands 202 and 204 may be subjected to motion, and the filler material may prevent the components of islands 202 and 204 from striking each other and causing damage. In at least some examples, the filler material may be a desiccant. Some example filler materials include silicone or other inert compounds.

FIG. 5B depicts another example configuration of islands 202, 204. In the example of FIG. 5B, second major opposing surfaces 212B, 214B are facing each other. With processing module 210 and circuit elements 208A-C in the configuration as depicted in FIG. 2, this means that processing module 210 and circuit elements 208A-C are disposed on the outside of the stacked circuit. In such examples no filler material may be disposed in space 230. However, to the extent that it is beneficial or necessary to keep processing module 210 and/or circuit elements 208A-C isolated from other parts of the implantable medical device, filler material may still be disposed in spaces 231 and 232. Again, in some of these examples, the filler material may be formed such that when the filler material is disposed within spaces 231, 232, the filler material folds around the components to isolate even the components on the same island section.

Figure 6A:
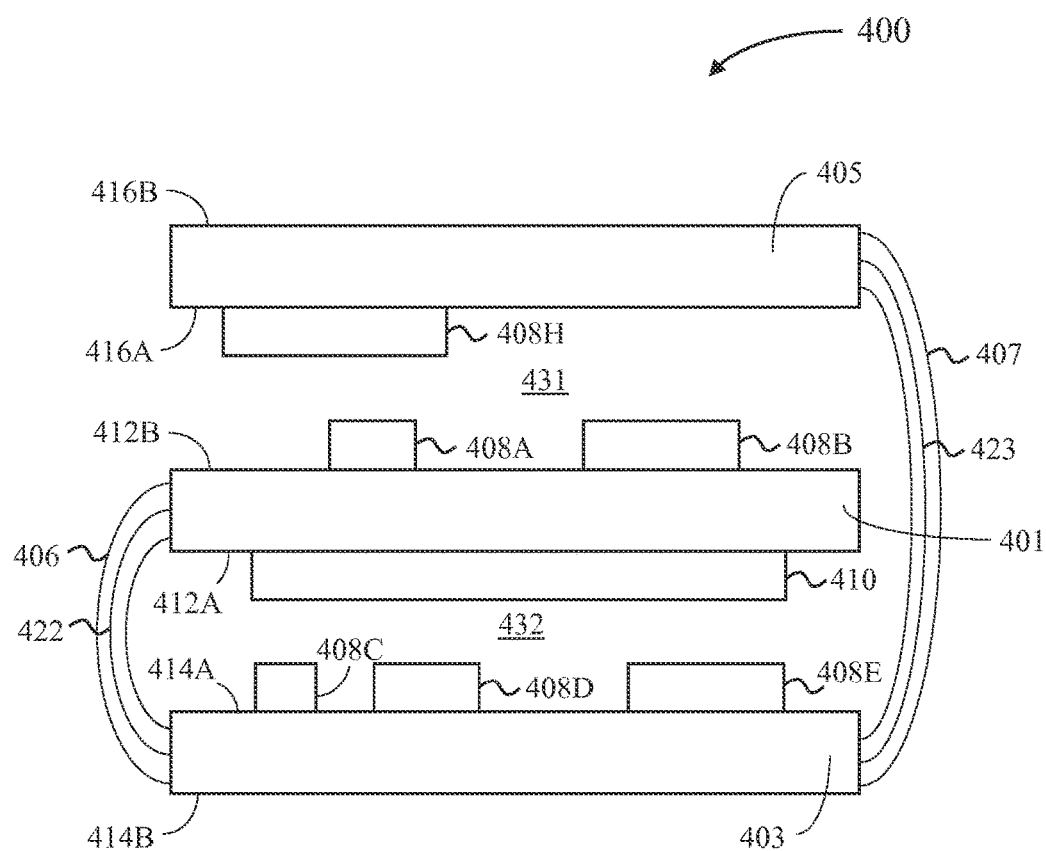
FIGS. 6A-C are example diagrams of orientations of another example electrical circuit, in accordance with aspects of the present disclosure.
Figure 6B:
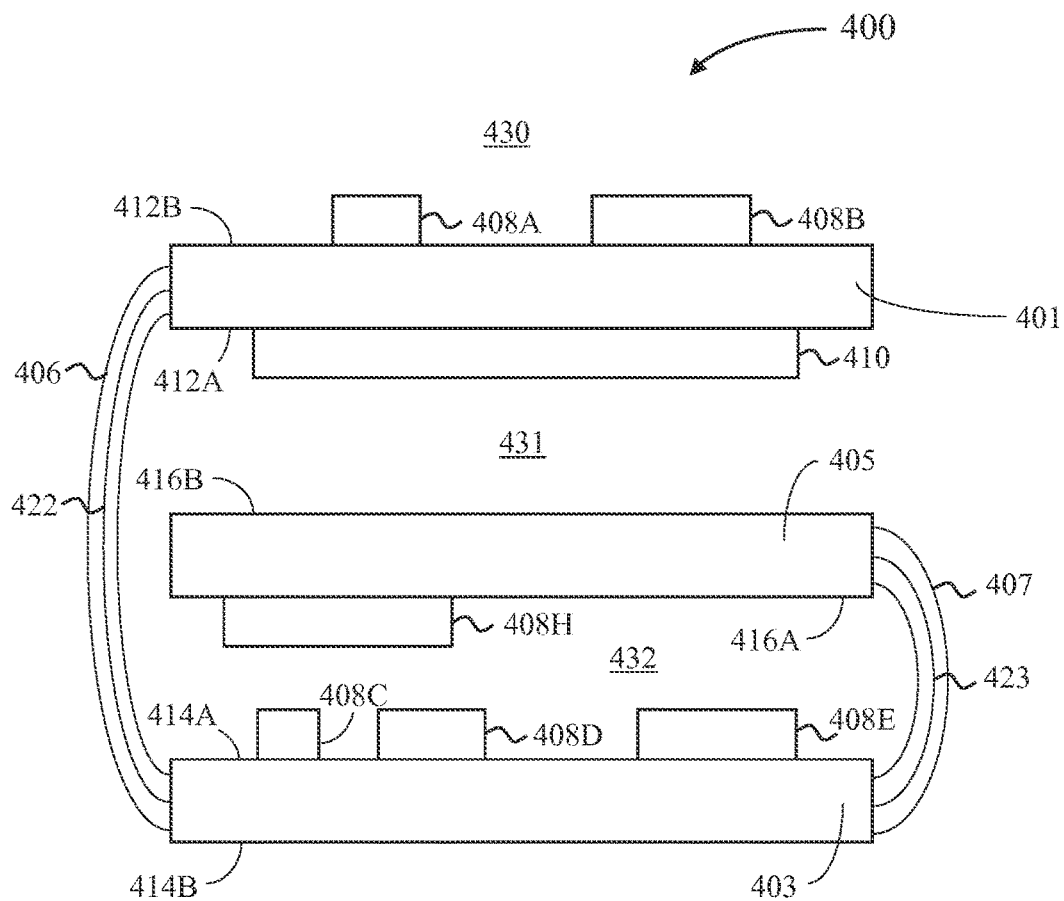
Figure 6C:
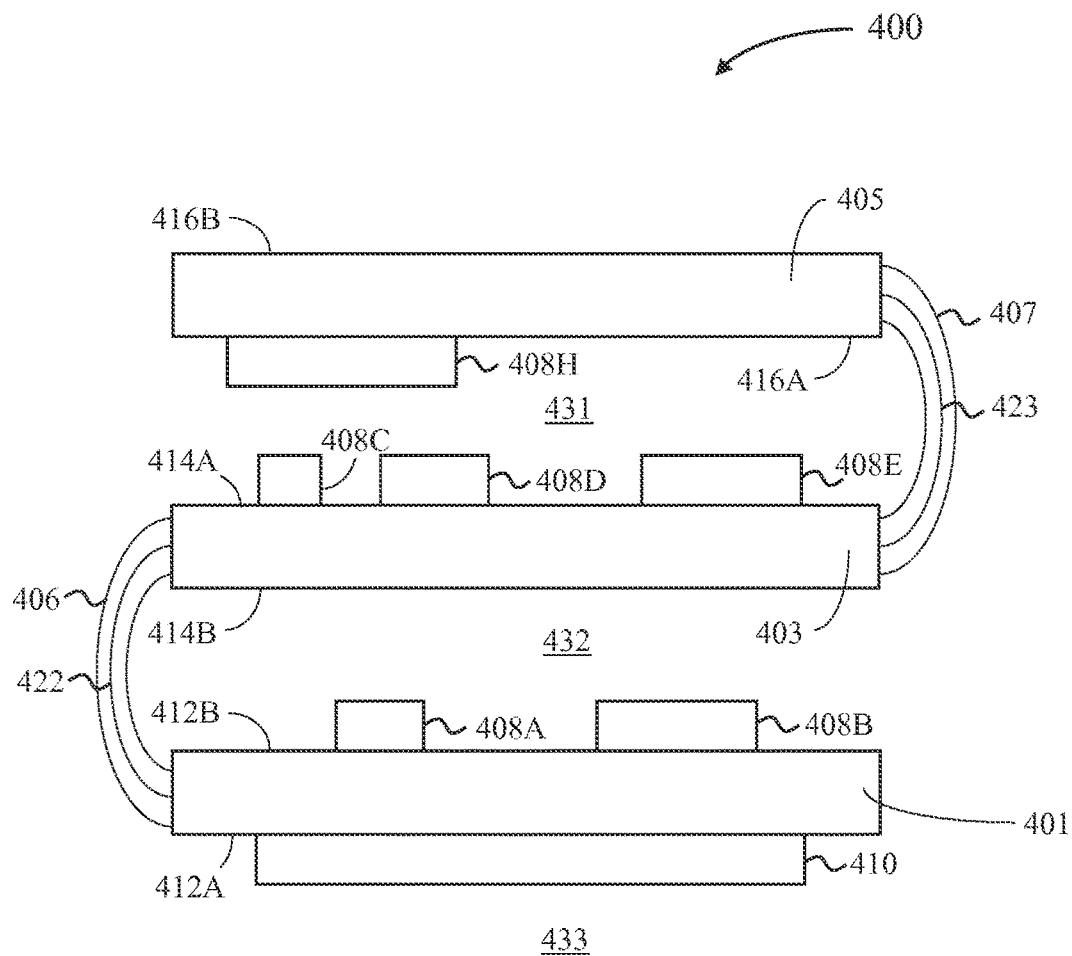

FIGS. 6A-C illustrate further example configurations that circuit 400 may take when disposed within an implantable medical device, such as LCP 100. In FIG. 6A, island sections 401, 403, and 405 are stacked with first major opposing surfaces 412A and 414A of island sections 401 and 403 facing each other and with second major opposing surface of island section 401 and first major opposing surface 416A facing each other. This configuration may be similar to that shown in the example of FIG. 4 where first ribbon section 406 is shorter than second ribbon section 407. The stacked configuration of FIG. 6A creates spaces 431 and 432 between island sections 405, 401 and island sections 401, 403, respectively.

In some examples, a filler material may be disposed within spaces 431 and 432 in order isolate processing module 410 and circuit elements 408A-H disposed on different island sections. In at least some examples, the filler material may be formed such that when the filler material is disposed within spaces 431 and/or 432, the filler material folds around the processing module 410 and/or circuit elements 408A-H to isolate even the components on the same island section. In some examples, the isolation that the filler material provides may be electrical isolation. For instance, the filler material may prevent the components on islands 401, 403, and/or 405 from contacting each other and causing a short circuit. In other examples, the filler material may instead, or additionally, provide mechanical isolation between the components of islands 401, 403, and/or 405. For instance, the device housing islands 401, 403, and/or 405 may be subjected to motion, and the filler material may prevent the components of islands 401, 403, and/or 405 from striking each other and causing damage. In at least some examples, the filler material may be a desiccant. Some example filler materials include silicone or other inert compounds.

In FIG. 6B, island sections 401, 403, and 405 are stacked with first major opposing surface 412A and second major opposing surface 416B of island sections 401 and 405, respectively, facing each other and with first major opposing surfaces 416A, 412A of island sections 403, 405 facing each other. In this configuration first ribbon section 406 may be longer than second ribbon section 407. The stacked configuration of FIG. 6B creates spaces 431 and 432 between island sections 405, 401 and island sections 403, 405, respectively. In some examples, a filler material may be disposed within spaces 431 and 432 in order isolate processing module 410 and circuit elements 408A-H disposed on different island sections. In at least some examples, the filler material may be formed such that when the filler material is disposed within spaces 431 and/or 432, the filler material folds around the processing module 410 and/or circuit elements 408A-H to isolate even the components on the same island section. In some examples, the isolation that the filler material provides may be electrical isolation. For instance, the filler material may prevent the components on islands 401, 403, and/or 405 from contacting each other and causing a short circuit. In other examples, the filler material may instead, or additionally, provide mechanical isolation between the components of islands 401, 403, and/or 405. For instance, the device housing islands 401, 403, and/or 405 may be subjected to motion, and the filler material may prevent the components of islands 401, 403, and/or 405 from striking each other and causing damage. In at least some examples, the filler material may be a desiccant. Some example filler materials include silicone or other inert compounds.

As depicted in FIG. 6B, some components may extend above the top of the stacked islands. In such examples, to the extent that it is beneficial or necessary to keep the components extending above the top isolated from other parts of the implantable medical device, the filler material may also be disposed in space 430. Again, in some of these examples, the filler material may be formed such that when the filler material is disposed within space 430, the filler material folds around the components to isolate even the components on the same island section.

In FIG. 6C, island sections 401, 403, and 405 are stacked with first major opposing surfaces 416A, 414A of island sections 405 and 403, respectively, facing each other and with second major opposing surfaces 414B, 412B of island sections 403, 401 facing each other. In this configuration first ribbon section 406 may generally be about the same length as second ribbon section 407. The stacked configuration of FIG. 6C creates spaces 431 and 432 between island sections 405, 403 and island sections 403, 401, respectively. In some examples, a filler material may be disposed within spaces 431 and 432 in order isolate processing module 410 and circuit elements 408A-H disposed on different island sections. In at least some examples, the filler material may be formed such that when the filler material is disposed within spaces 431 and/or 432, the filler material folds around the processing module 410 and/or circuit elements 408A-H to isolate even the components on the same island section. In some examples, the isolation that the filler material provides may be electrical isolation. For instance, the filler material may prevent the components on islands 401, 403, and/or 405 from contacting each other and causing a short circuit. In other examples, the filler material may instead, or additionally, provide mechanical isolation between the components of islands 401, 403, and/or 405. For instance, the device housing islands 401, 403, and/or 405 may be subjected to motion, and the filler material may prevent the components of islands 401, 403, and/or 405 from striking each other and causing damage. In at least some examples, the filler material may be a desiccant. As depicted in FIG. 6C, some components may extend above the top of the stacked islands—e.g. processing module 410. In such examples, to the extent that it is beneficial or necessary to keep the processing module 410 isolated from other parts of the implantable medical device, filler material may also be disposed in space 433. Again, in some of these examples, the filler material may be formed such that when the filler material is disposed within space 433, the filler material folds around the components to isolate even the components on the same island section. Some example filler materials include silicone or other inert compounds.

Of course, these are only a few examples of stacked configurations that island sections 401, 403, and 405 may take. In other examples, island section 403 may be in the middle of the stack with island section 401 on top and island section 405 on bottom. In still further examples, the locations of processing module 410 and circuit elements 408A-H may differ, or the island sections may include additional or different components, e.g. various mechanical/physiological/biological sensors such as an accelerometer, a posture sensor, heart sounds sensor, or the like. Accordingly, the stacked configuration of these different examples may look different than depicted in FIGS. 6A-6C, or the dimensions of the stacked configurations may differ to accommodate the various different components.

Figure 7:
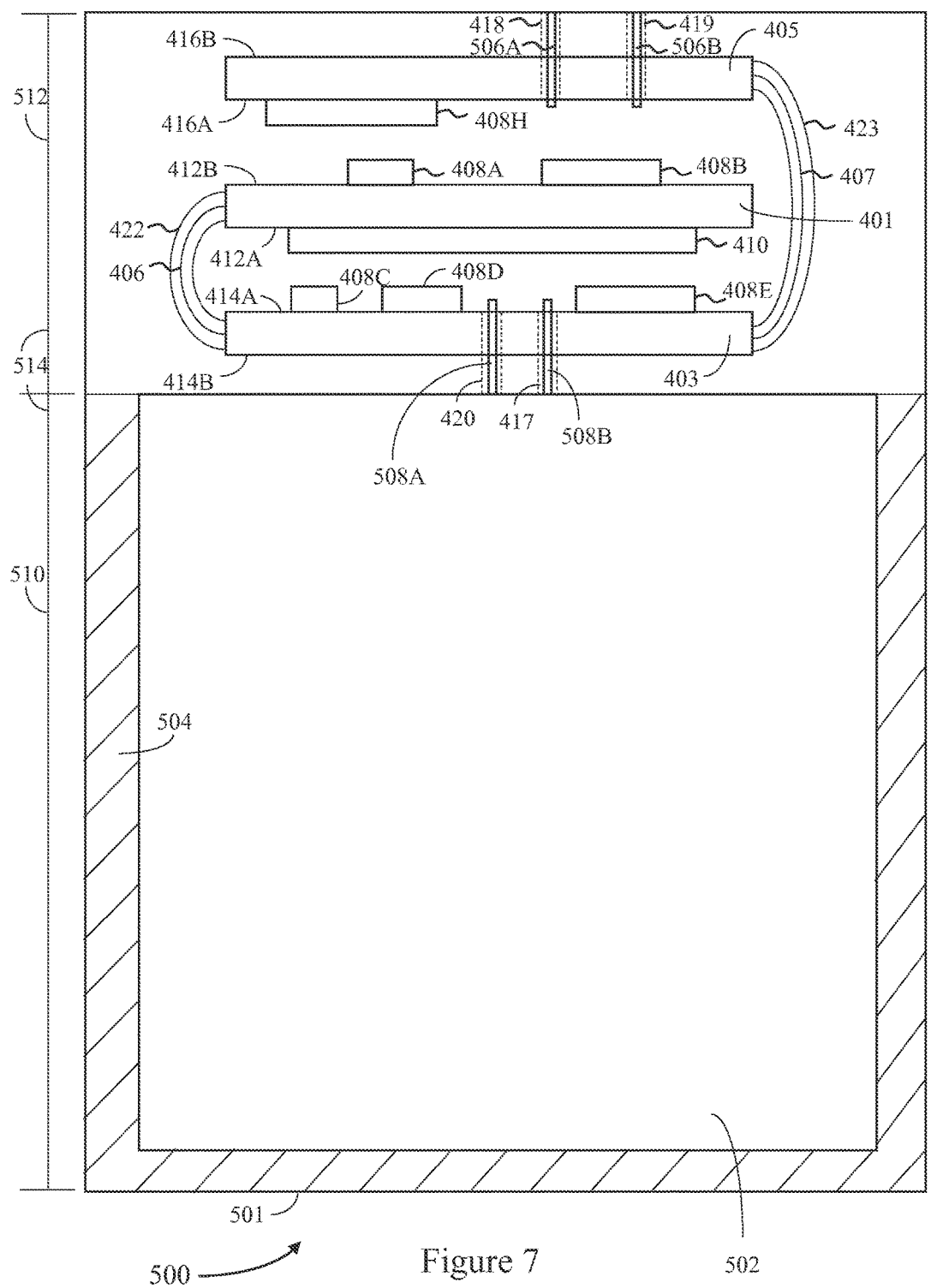
FIG. 7 is schematic of an example orientation of internal components of an implantable medical device, in accordance with aspects of the present disclosure.

FIG. 7 is an illustrative cross-section of an exemplary implantable medical device with example circuit 400 in the configuration of FIG. 6A disposed within the implantable medical device. Implantable medical device 500 may include circuit 400 along with energy storage device 502. Both circuit 400 and energy storage device 502 may be hermetically sealed within housing 501. In some examples, circuit 400 may generally be stacked on top of energy storage device 502, as illustrated in FIG. 7. Implantable medical device 500 may also include interconnect 506A, 506B and 508A, 508B. Interconnects 506A, 506B may generally extend into or through feedthroughs 418 and 419. Interconnects 506A, 506B may be connected to electrode(s) external to housing 501 and/or directly to housing 501, thereby electrically connecting the electrode(s) and/or housing 501 to circuit 400. Interconnects 508A, 508B may be connected to an electrode, housing 501, and/or energy storage device 502, thereby electrically connecting the electrode, housing 501, and/or energy storage device 502 to circuit 400. In some examples, implantable medical device 500 may further include insulation 504 lining housing 502 to electrically isolate energy storage device 502 from housing 504 and, in some examples, other internal components of implantable medical device 500.

Implantable medical device 500 may generally have a height 514 as illustrated in FIG. 7. When measuring along this height dimension, energy storage device 502 may extend for a length 510 and circuit 400 may extend for a length 512. Some example values for height 510 may range from eight millimeters to twenty-five millimeters, and in some examples height 510 may be fourteen millimeters. Some example values for height 512 may range from one millimeter to five millimeters, and in some examples height 512 may be two millimeters. Percentages may be another way to describe the relative portions of implantable medical device 500 that circuit 400 and energy storage device 502 take up. For instance, the height that energy storage device 502 extends within implantable medical device 500 may be between fifty percent and ninety-five percent of the total height of implantable medical device 500, or height 514. In some examples, energy storage device 502 may extend within implantable medical device 500 for eighty percent of height 512. Additionally, the height that circuit 400 may extend within implantable medical device 500 may be between five percent and fifty percent of height 514. In some additional examples, circuit 400 may extend within implantable medical device 500 for twenty percent of height 514. Although FIG. 7 is depicted with circuit 400 disposed within implantable medical device 500, in other examples implantable medical device 500 may include circuit 200 disposed within housing 501 and stacked on top of energy storage device 502.

Figure 8:
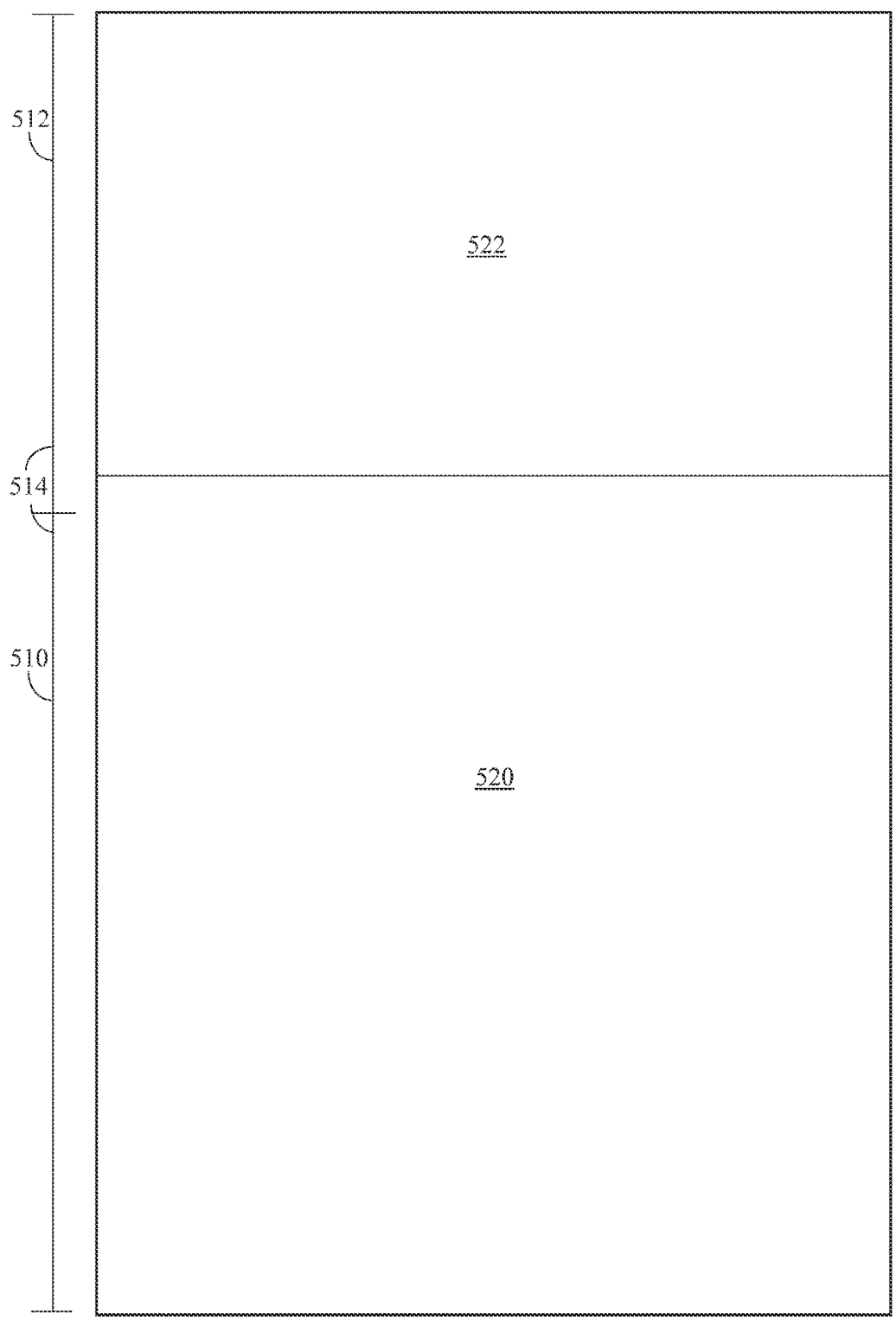
FIG. 8 is an example illustration of various sections of an implantable medical device, in accordance with aspects of the present disclosure.

FIG. 8 is another illustration depicting example implantable medical device 500. Although FIG. 8 does not show the internal components of implantable medical device 500, implantable medical device 500 has been partitioned into two sections, section 520 and section 522. The boundary between sections 520, 522 represents the boundary between energy storage device 502 and the circuit stacked on top of implantable medical device 500, e.g. a circuit such as circuit 200 or circuit 400, within implantable medical device 500. Each section 520, 522 may be thought of as encompassing a certain volume of implantable medical device 500. That is, if a plane bisected implantable medical device 500 perpendicular to the height dimension along the boundary between sections 520, 522, the resulting portions of implantable medical device 500 would have defined volumes. In some examples, the volume of section 520 may range between fifty percent and ninety percent of the total volume of implantable medical device 500. Additionally, in some examples, the volume of section 522 may range between ten percent and fifty percent of the total volume of implantable medical device 500. Accounting for any insulation or other components situated around energy storage device 502, energy storage device may take up between eighty-five percent and ninety-five percent of the volume of section 520, which translates to between forty-two and a half percent and eighty-five and a half percent of the total volume of implantable medical device 500. Accounting for any empty space between the islands of the circuit disposed within implantable medical device 500, the circuit may take up between fifty and eighty percent of the volume of section 522. If the circuit includes filler material, the total volume that the circuit and the filler material take up may range as high as ninety-five percent of the volume of section 522. This translates to the circuit taking up between five percent and forty-seven and a half percent of the total volume of implantable medical device 500.

Figure 9A:
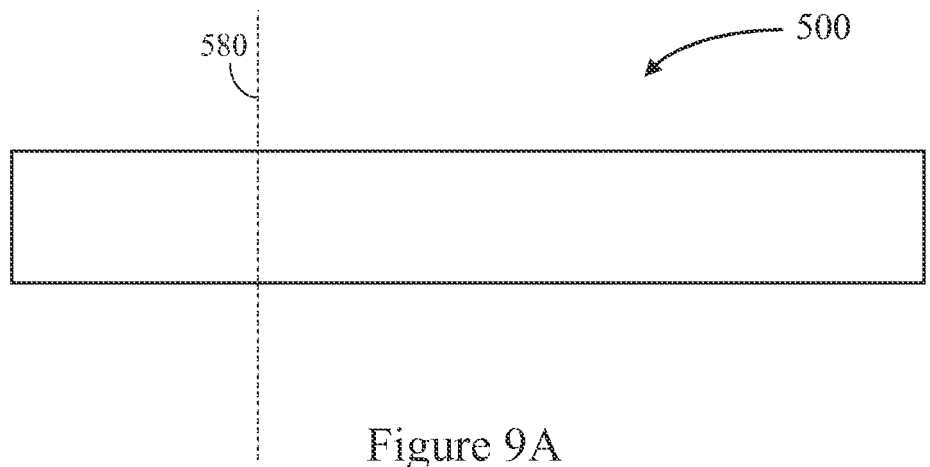
FIG. 9A is side view of an example implantable medical device.
Figure 9B:
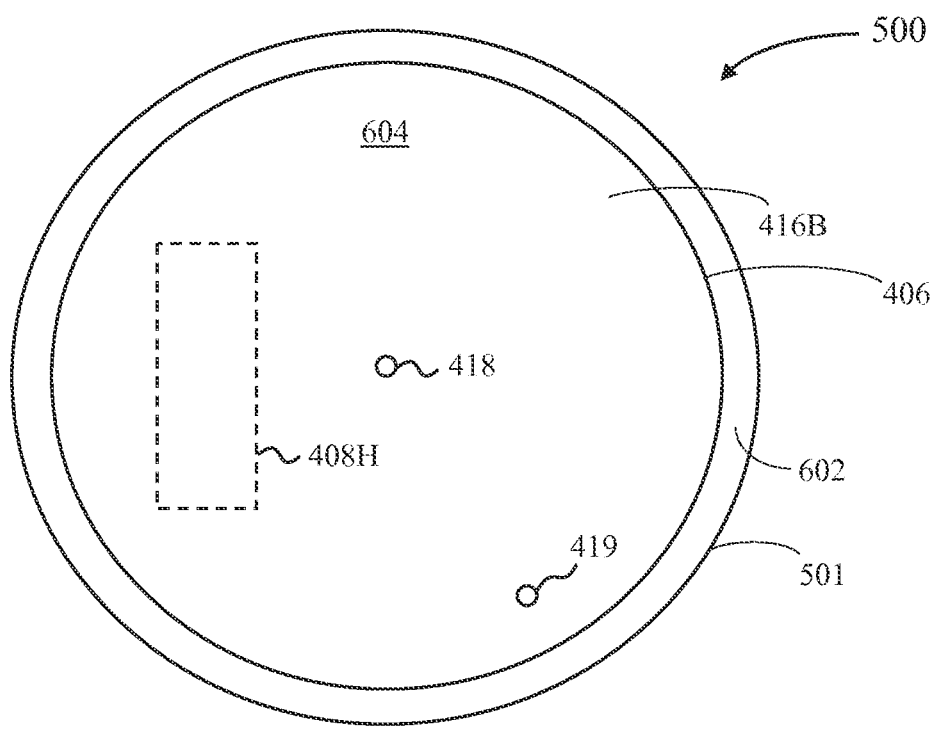
FIG. 9B is perspective view of a cross section of an example medical device, in accordance with aspects of the present disclosure.

FIG. 9A depicts a side-view of implantable medical device 500. FIG. 9B depicts a cross section of implantable medical device 500 as viewed in a plane parallel to line 580 of FIG. 9A. In FIG. 9B, housing 501 can be seen surrounding the internal components of implantable medical device 500. Specifically, the main internal component visible in FIG. 9B include island 406 of circuit 400, and more specifically second major opposing surface 416B of circuit 400. This may be the case when circuit 400 is disposed within implantable medical device 500 in the configuration depicted in FIG. 6A. When viewed from the perspective of FIG. 9B, housing 501 may define a cross section area 602. Second major opposing surface 416B of island 406 may also define a cross section area 604, e.g. the area of second major opposing surface 416A. In some examples, cross section area 604 may range between seventy and ninety-five percent of cross section area 602. In some specific examples, cross section area may be eighty percent or ninety percent of cross section area 602.

In some examples, circuits 200 and/or 400 may be fabricated using a multi-stage fabrication process. First, conductive traces may be laid down on a substrate that is larger than the final circuit, such as a PCB or other acceptable substrate. Next, the various components, e.g. a processing module and plurality of circuit elements, may be bonded to the substrate in a specific pattern relative to the conductive traces to electrically connect the various components in a desired configuration. In some instances, when the traces are laid down, extra traces may be laid down for testing purposes. The extra traces may terminate in a testing pad, such as an array of aligned traces or pads that may be easily connected to an external device. The circuit components, e.g. the processing module and the circuit elements may then be tested to ensure that they are functioning properly by an external device connected to the testing pad. If the circuit passes the testing, the circuit may then be excised from the substrate and the extra traces and testing pad, thereby resulting in the final circuit, e.g. circuit 200 or 400 as depicted in FIGS. 2 and 4.

Although described above with respect to an LCP, other examples may include devices other than an LCP utilizing the disclosed devices and techniques. For example, any implantable medical device may benefit from the disclosed circuits. Some other example devices include a dedicated sensing device that does not include stimulation capabilities, such as a loop recorder, pressure sensor, and diagnostic devices (including subcutaneously implanted diagnostic devices). Additionally, other types of stimulation devices may benefit from the disclosed devices and techniques. For example, microstimulators other than for cardiac applications, neurostimulators, including devices designed to stimulate nerves such as the vagus nerve, or the hypoglossal nerve, and other devices that may be designed to stimulate various baroreceptors are all examples of devices that may be used with the disclosed circuits and techniques.

Those skilled in the art will recognize that the present disclosure may be manifested in a variety of forms other than the specific examples described and contemplated herein. For instance, as described herein, various examples include one or more modules described as performing various functions. However, other examples may include additional modules that split the described functions up over more modules than that described herein. Additionally, other examples may consolidate the described functions into fewer modules. Accordingly, departure in form and detail may be made without departing from the scope and spirit of the present disclosure as described in the appended claims.

What is claimed:

1. An implantable medical device (IMD) configured for implantation within a patient, the IMD comprising:
    an elongated housing having a major and minor dimension;
    two or more electrodes electrically exposed outside of the housing;
    an energy storage device disposed within the housing, the energy storage device having a feedthrough extending away from the energy storage device along the major dimension of the elongated housing;
    a flexible circuit disposed within the housing and electrically connected to the energy storage device and the two or more electrodes;
    the flexible circuit comprises a flexible substrate that has two or more island sections and one or more ribbon sections, wherein each island section is electrically connected to at least one other island section by one or more ribbon section, wherein each island section has two opposing major surfaces, and wherein each ribbon section comprises a metal portion bonded between two polymer portions, and each of the island sections comprises a first metal portion bonded between two polymer portions, and second metal portions bonded to the two polymer portions;
    a first one of the two or more island sections and a second one of the two or more island sections being stacked within the housing such that the two opposing major surfaces of the first one of the two or more island sections and the two opposing major surfaces of the second one of the two or more island sections extend transverse to the major dimension of the elongated housing; and
    the first one of the two or more island sections and the second one of the two or more island sections positioned within the elongated housing adjacent to the energy storage device such that one of the first island section and the second island second receives the feedthrough of the energy storage device.

* * * * *